US006552787B1

(12) United States Patent
Potyrailo et al.

(10) Patent No.: US 6,552,787 B1
(45) Date of Patent: Apr. 22, 2003

(54) RAPID NON-DESTRUCTIVE SCREENING METHODS FOR POLYMERIC COATINGS AND MATERIALS

(75) Inventors: Radislav Alexandrovich Potyrailo, Niskayuna, NY (US); James Edward Pickett, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 179 days.

(21) Appl. No.: 09/677,449

(22) Filed: Sep. 29, 2000

(51) Int. Cl.$^7$ .............................................. G01N 21/64
(52) U.S. Cl. .................. 356/317; 250/458.1; 250/461.1
(58) Field of Search ................. 356/317, 318, 356/417; 250/458.1, 459.1, 461.1

(56) References Cited

U.S. PATENT DOCUMENTS

| | | | |
|---|---|---|---|
| 4,839,405 A | 6/1989 | Speelman, et al. | 524/99 |
| 5,605,761 A | 2/1997 | Burns, et al. | 482/412 |
| 5,705,600 A | 1/1998 | Jones, et al. | 528/298 |
| 5,759,689 A | 6/1998 | Sieloff | 428/412 |
| 5,816,238 A | 10/1998 | Burns et al. | 126/569 |
| 5,856,486 A | 1/1999 | Pickett et al. | 544/385 |
| 5,866,658 A | 2/1999 | Talkowski | 525/183 |
| 5,869,554 A | 2/1999 | Pickett et al. | 524/99 |
| 5,916,997 A | 6/1999 | Webb et al. | 528/194 |

OTHER PUBLICATIONS

Pickett, J.E.; Webb, K.K., Calculated and measured outdoor UV doses, Die Angewandte Makromolekulare Chemie. 1997, 252, 217–236.

Pickett, J.E.; P., B.J.; Oliver, R.J., Effect of accelerated exposure conditions on the photodegradation of BPA polycarbonate/ABS blends, Die Angewandte Makromolekulare Chemie 1997, 247, 1–18.

Pickett, J.E.; Moore, J.E., Photodegradation of UV absorbers: kinetics and structural effects, Makromol. Chem. 1995, 232, 229–238.

Humphrey, J. S.; Schultz, A. R.; Jaquiss, D.B.; Flash photochemical studies of polycarbonate and related model compounds, photodegradation vs. photo–Fries rearranemeanat, Macromolecules 1973, 6, 305–314.

Hoyle, C. E. ; Shah, H; G. L., Photochemistry of bisphenol–A based polycarbonate: the affect of the matrix and early detection of photo–Fries product formation. J. Polym. Sci. A: Polym. Sci. A: Polym. Chem.1992, 30,1525–1533.

Shah, H. ; Rufus, I.B. ; Hoyle , C.E., Photochemistry of bisphenol–A–based polycarbonate: early detection of photoproducts by fluorescence spectroscopy, Macromolecules 1994, 27, 553–561.

Hoyle, C.E.; Rufus, I.B.; Shah, H., Solvent effect on the photophysics of bisphenol–A–based polycarbonate and diphenylcarbonate, Can. J. Chem. 1995, 73, 2062–2068.

Pankasem, S.; Kuczynski, J.; Thomas J. K., Photochemistry and photodegradation of polycarbonate, Macromolecules 1994, 27, 3773–3781.

(List continued on next page.)

*Primary Examiner*—F. L. Evans
(74) *Attorney, Agent, or Firm*—Noreen C. Johnson; Christian G. Cabou

(57) ABSTRACT

This invention provides a method for the rapid determination of the light-induced degradation of polymeric materials and coatings. In a preferred embodiment of this method, samples are exposed to UV light and fluorescence emission spectral data are collected and fluorescence properties such as wavelength, intensity, lifetime, and polarization are monitored for changes, which in turn are an indication of the weatherability of a given sample.

22 Claims, 11 Drawing Sheets

OTHER PUBLICATIONS

Rufus, I.B.; Shah, H.; Hoyle, C.E., Identification of fluorescent products produced by the thermal treatment of bisphenol–A–based polycarbonate, J. Appl. Polym. Sci. 1994, 51, 1549–1558.

Potyrailo, R.A.; Lemmon, J.P. Method for direct measurement of polycarbonate compositions by fluorescence; GE CRD Patent Docket RD–27,022, U.S. Ser. No. 09/398,678 Filed Sep. 20,1999.

Factor, A., Search for the Sources of Color in Thermally Aged, Weathered and γ–Ray Irradiated Bisphenol A Polycarbonate, International Conference on Advances in the Stabilization and Degradation of Polymers, 37–53.

Chipalkatti, M.H.; Laski, J.J., Investigation of Polycarbonate Degradation by Fluorescence Spectroscopy and Its Impact on Final Performance, American Chemical Society, Advances in Chemistry Series, 1993, 623–642.

Factor, A., Degradation of Bisphenol A Polycarbonate by Light and γ–Ray Irradiation, Handbook of Polycarbonate Science and Technology, 267–292.

RAPID NON-DESTRUCTIVE SCREENING METHODS FOR POLYMERIC COATINGS AND MATERIALS

BACKGROUND OF THE INVENTION

This invention relates to methodology for the rapid non-destructive screening of samples of polymer composites and coatings. In particular, it relates to a method for the rapid determination of the light-induced degradation of polymeric materials and coatings. Additionally, the methodology may be applied to combinatorial libraries of such composites and coatings.

A significant factor in the outdoor weathering lifetime of a polymeric material is the ultraviolet radiation (UV) dosage received by a given sample. Although outdoor weathering data is considered most useful for the direct evaluation of a material's UV stability, the fundamental limitation of such techniques is the need for multi-year exposure times. Thus, other weathering approaches are also used as a more attractive alternative to more rapidly evaluate and qualify materials for particular applications in an effort to judge acceptable performance of the polymer or coating as well as screening additives to optimize efficacy.

Outdoor weathering studies are typically performed at test sites in Florida or Arizona for durations of about one to ten years. Reductions in testing times can be achieved by using accelerated laboratory methods such as ASTM G-26 xenon arc lamp conditions. Even running at high irradiance, it takes about 1100 h of sample exposure to accumulate 2700 kJ/m$^2$ at 340 nm which is approximately equivalent to one year of Florida exposure. Thus, laboratory accelerated weathering generally provides acceleration factors of 3 to 10 for most materials.

Degradation of organic materials such as polymers and coatings by ultraviolet light is often manifested by a loss in gloss and/or a yellowing in color, especially in white pigmented materials. A widely used analytical technique for determination of UV degradation involves measurements of the Yellowness Index (YI) according to ASTM procedure D-1925. Accordingly, a lower change in YI ($\Delta$YI) suggests higher photostability of a sample, and thus better weatherability. However, for reliable quantification, it is desirable to reach a $\Delta$YI value of 3 or more, which often corresponds to at least several hundred kJ/m$^2$ of irradiation at 340 nm. Moreover, reliable measurements of YI cannot be performed after short exposure times, i.e., several hours, because of the relatively low sensitivity of YI determination at low UV exposures.

An additional 10–1000 fold acceleration of the weatherability studies is needed for analysis of multiple samples such as those created as combinatorial libraries. Unfortunately, currently available analytical methods lack the sensitivity to detect sample properties such as YI and others after only several hours of UV exposure and correlate them with the ultimate weatherability of the sample. Moreover, the color shift in black or darkly colored samples is often relatively insensitive to UV exposure. Color measurement in other samples containing pigments and dyes can be complicated by color shifts in the colorants themselves. Thus, often only gloss retention measurements are done on dark and black samples, which usually require even larger UV exposure doses for reliable determinations of a given sample's UV stability, since often gloss loss is apparent only after the surface is heavily degraded.

Thus, it would be desirable to develop a method for reliable quantification of weatherability of different types of samples, including dark and black materials, at exposure times of only hours. In addition, it would be desirable to be able to calculate the useful lifetime of a given material.

BRIEF SUMMARY OF THE INVENTION

This invention provides a method for the rapid determination of the light-induced degradation of polymeric materials and coatings. In this method, samples are exposed to UV light and fluorescence emission spectral data are collected and fluorescence properties such as wavelength intensity, lifetime and polarization are monitored for changes, which in turn are an indication of the weatherability of a given sample.

DETAILED DESCRIPTION OF THE INVENTION

Figure 1:
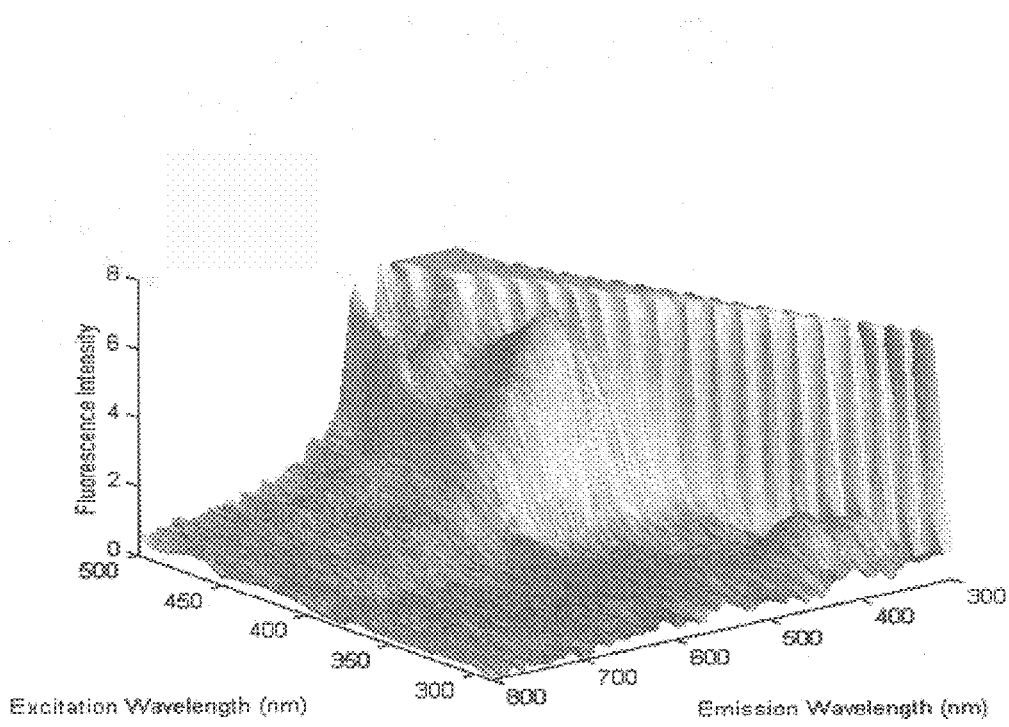
FIG. 1 is a plot of the excitation-emission spectra of a polycarbonate sample containing 2% rutile TiO$_2$ before exposure to UV radiation.

This invention describes the use of fluorescence spectroscopy and imaging for the rapid determination of the light-induced degradation of polymeric materials and coatings. This methodology is based on the excitation and concomitant fluorescence in a single sample or an array of samples over a preselected wavelength range and the collection of the emission intensity or other fluorescence property such as lifetime, wavelength, or polarization with a suitable photodetector. Because fluorescence light is isotropic, there is no need to use an integrating sphere for its collection as is the case in color determination. Moreover, the measurements can be performed on samples of any color, including highly colored and black samples. In a preferred embodiment, the materials so analyzed will be those which contain substances comprised of aromatic moieties which are susceptible to light-induced, especially UV light-induced degradation.

Thus, in a first embodiment, the present invention provides a method for determining the weatherability of at least one sample, wherein said sample absorbs ultraviolet and/or visible light and fluoresces ultraviolet, visible, and/or near infrared light, which comprises:

(a) exposing said sample to ultraviolet radiation while compiling fluorescence emission spectral data from said sample over a period of time beginning after initial exposure; and (b) applying a pre-determined selection test to said spectral data so as to indicate which of the samples exhibit a desired resistance to ultraviolet radiation-induced degradation.

In this method, we have found that while utilizing the instrumentation as set forth in the examples below, at least about 3 kJ/m$^2$ at a signal to noise ratio (s/n) of about 3 is necessary to provide meaningful data which can be analyzed in the determination of the weatherability of a sample. As one of ordinary skill in the art would recognize, this required dosage level is a function of the sin capabilities of the detection instrumentation and will thus decrease as the sensitivity of the instrumentation and hence the s/n ratio increases. In addition, the composition and pigmentation of the sample will determine the amount of exposure required to generate a detectable fluorescence signal.

In a further embodiment, the spectral data so compiled may be utilized to calculate the useful lifetime of a given sample based on its capacity for resistance to UV degradation. Accordingly, as a further aspect of the invention, there is provided the above method, further comprising the step of calculating the useful lifetime of a given sample material based on said spectral data. For example, if the rate of increase in fluorescence intensity for a sample containing stabilizer is one half of the rate of an otherwise identical but unstabilized sample, and the useful lifetime of the unstabilized sample is known, the useful lifetime of the stabilized sample should be twice that of the unstabilized sample.

In this context, the term "weatherability" denotes the tendency for a given sample to degrade based on its polymeric component(s), coloration and/or pigmentation, and the presence or absence of the various typical polymer additives.

The spectral data chosen to be analyzed may be any combination of the change in fluorescence intensity, fluorescence stokes shift, fluorescence lifetime, and polarization.

Polarization detection can be used for evaluating the formation of new fluorescence species. It can be performed by exciting the sample with a plane polarized light and observing the depolarization of fluorescence emission. These measurements can be performed on solid samples at different temperatures, including that above the glass transition temperature ($T_g$) of polymer or using a polymer dissolved in a suitable solvent.

Thus, in a preferred embodiment, the present invention provides a method for determining weatherability of at least one sample, wherein said sample absorbs visible and/or ultraviolet light and fluoresces visible, ultraviolet, and/or near infrared light, which comprises:

(a) exposing said sample(s) to ultraviolet radiation while compiling fluorescence emission spectral data from said sample over a period of time beginning after initial exposure; and (b) applying a pre-determined selection test to said spectral data so as to indicate which of the samples exhibits the least amount of increase of fluorescence intensity and/or slowest rate of fluorescence increase.

In a further preferred embodiment, the present invention provides a method for determining weatherability of at least one sample, wherein said sample absorbs visible and/or ultraviolet light and fluoresces visible, ultraviolet, and/or near infrared light, which comprises:

(a) exposing said sample to ultraviolet radiation while compiling fluorescence emission spectral data from said sample over a period of time beginning after initial exposure; and (b) applying a pre-determined selection test to said spectral data so as to indicate which of the samples exhibits the least amount of change in fluorescence stokes shift.

As used herein, the term "fluorescence stokes shift" refers to the difference in wavelength between absorption and fluorescence maxima, which for a given fluorophore will be constant.

In a further preferred embodiment of the invention, an array of samples which represent a large, designed experimental sampling based on, for example, variations in polymer composition, pigment, pigment loading, and the presence or absence of various polymer additives and stabilizers and variation of concentration of such additives, stabilizers and processing conditions are simultaneously irradiated with ultraviolet radiation and spectral data is compiled over time. After collection of initial data, one or more preselected spectral data may be chosen in order to identify and classify those samples which exhibit a desired level of resistance to ultraviolet light-induced degradation, thus indicating which features of a given sample provide the desired resistance to UV degradation.

In such samples, various polymer and coatings additives are well known. As to pigments, the known inorganic and organic pigments may be utilized. For example, such pigments may be titanium dioxide, carbon black and iron oxide pigments. Further examples of such pigments may be found in Color Index, 3 Ed., 2d Rev., 1982, published by the Society of Dyers and Colorists in association with the American Association of Textile Chemists and Colorists. Specific examples include CI Pigment White 6 (titanium dioxide); CI Pigment Red 101 (red iron oxide); CI Pigment Yellow 42, CI Pigment Blue 15, 15:1, 15:2, 15:3, 15:4 (copper phthalocyanines); CI Pigment Red 49:1, and CI Pigment Red 57: 1.

The fluorescence detection method of the present invention makes possible a more detailed study of samples because different excitation-emission conditions can be selected when different fluorescent species in a given sample are preferentially excited at different wavelengths. Such methodology is especially useful when different stabilizers, flame retardant compounds, and other additives are present in the analyzed material. In this fashion, large arrays of samples constituting a designed experiment may be evaluated in a relatively short period of time.

Because the isotropic nature of the fluorescence emission, these arrays of samples may be measured simultaneously by fluorescence imaging. In such a case, the entire array or library is irradiated with UV light and the fluorescence spectral data is collected with an imaging detector. As a light source, any commercially available lamp or laser may be utilized, provided such source emits the desired wavelengths and intensity, and as a detection device, any commercially available device typically used to detect fluorescence emissions may be utilized. Preferably the light exposure of steps (a), above, are at wavelengths of greater than 295 nm.

Unlike other detection methods, such as color and gloss retention measurements, the use of fluorescence detection has several fundamental advantages:

1. We have found that in the case of the UV degradation of polycarbonate and other polymer samples having aromatic moieties, degradation products generate more fluorescence than unexposed samples. Thus, fluorescence measurements are inherently more sensitive than color measurements.
2. A single technique for highly sensitive measurements of light and dark samples at low exposure levels is provided.
3. Fluorescence measurement does not require the use of an integrating sphere for signal collection because fluorescence light distribution is isotropic.
4. Possibility for measurement of multiple samples simultaneously by irradiating an array of samples with an excitation light and collecting the emission parameters (fluorescence intensity, wavelength, lifetime, or polarization) independently from each sample with an imaging detector system.
5. Detailed study of materials with different fluorescence excitation-emission conditions for preferential excitation of different species.

As described herein, the sample(s) may include any suitable thermoplastic or thermoset resin. For example, the sample(s) may include polycarbonates, polyesters, polystyrenes, styrene-acrylonitrile (SAN) copolymers, acrylonitrile-butadiene-styrene (ABS) copolymers, acrylonitrile-styrene-acrylate (ASA) copolymers, polyarylates, and blends thereof.

EXPERIMENTAL SECTION

EXAMPLE 1

Excitation-emission Fluorescence Mapping of Weatherable Materials.

Fluorescence properties of weatherable materials before and after the exposure to UV radiation were investigated with different excitation-emission conditions. Fluorescence maps were constructed using samples of Lexan® 140 polycarbonate containing 2% of $TiO_2$ pigment. Measurements were performed on a setup which included a white light source (450-W Xe arc lamp, SLM Instruments, Inc., Urbana, Ill., Model FP-024), a monochromator for selection of the excitation wavelength (SLM Instruments, Inc., Model FP-092), and a portable spectrofluorometer (Ocean Optics, Inc., Dunedin, Fla., Model ST2000). The spectrofluorometer was equipped with a 200-um slit, 600-grooves/mm grating blazed at 400 mm and covering the spectral range from 250 to 800 nm with efficiency greater than 30%, and a linear CCD-array detector. Excitation light from the monochromator was focused into one of the arms of a "six-around-one" bifurcated fiber-optic reflection probe (Ocean Optics, Inc., Model R400-7-UV/VIS). Emission light was collected from a sample when the common end of the fiber-optic probe was positioned near the sample at a certain angle to minimize the amount of excitation light reflected from the sample back into the probe. The second arm of the probe was coupled to the spectrofluorometer.

Figure 2:
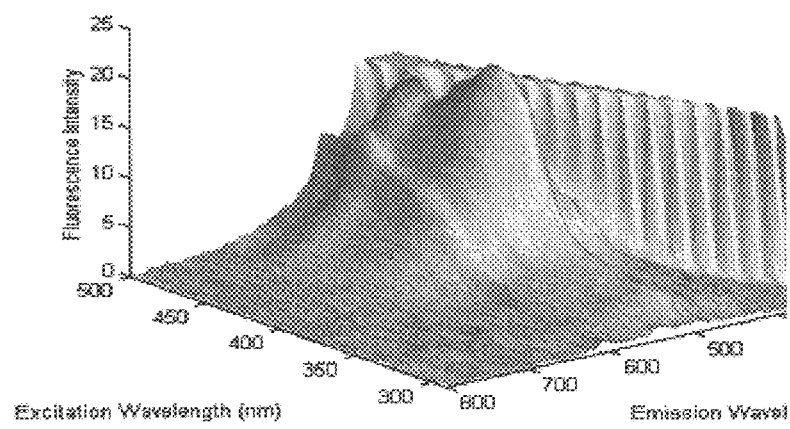
FIG. 2 is a plot of the excitation-emission spectra of a polycarbonate sample containing 2% rutile TiO$_2$ after 806 h of exposure to UV-A ultraviolet radiation (340 nm wavelength) during a QUV test.
Figure 3:
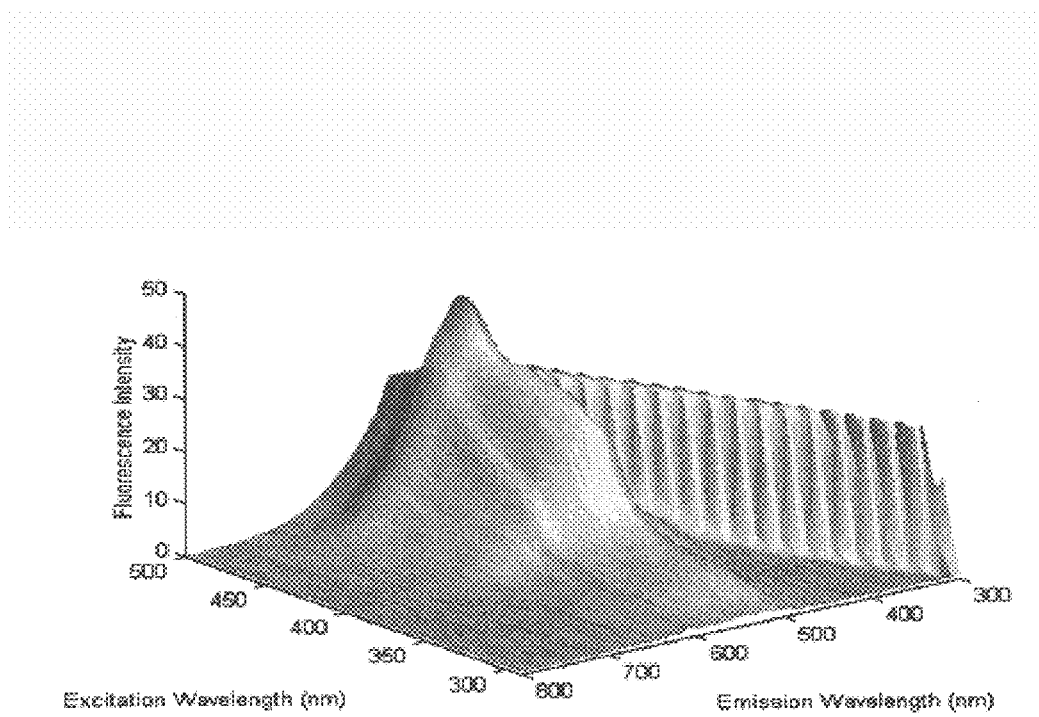
FIG. 3 is a plot of the excitation-emission fluorescence spectra of a polycarbonate sample containing 2% rutile TiO$_2$ at the terminal state.

FIGS. 1–3 demonstrate the difference in the fluorescence excitation-emission spectra of $PC+2\%TiO_2$ before exposure to UV radiation, after 806 h of exposure to UV radiation during a QUV-A test, and at its terminal state. These differences are twofold. First, the overall maximum intensity of fluorescence increases upon sample degradation from about 8 to about 50. Second, the relative intensities of certain fluorescence peaks are changing upon sample degradation. For example, two emission peaks at 500 nm corresponding to 400 and 450 nm of excitation light dramatically change their ratio as the sample is degraded to its terminal state.

Figure 4:
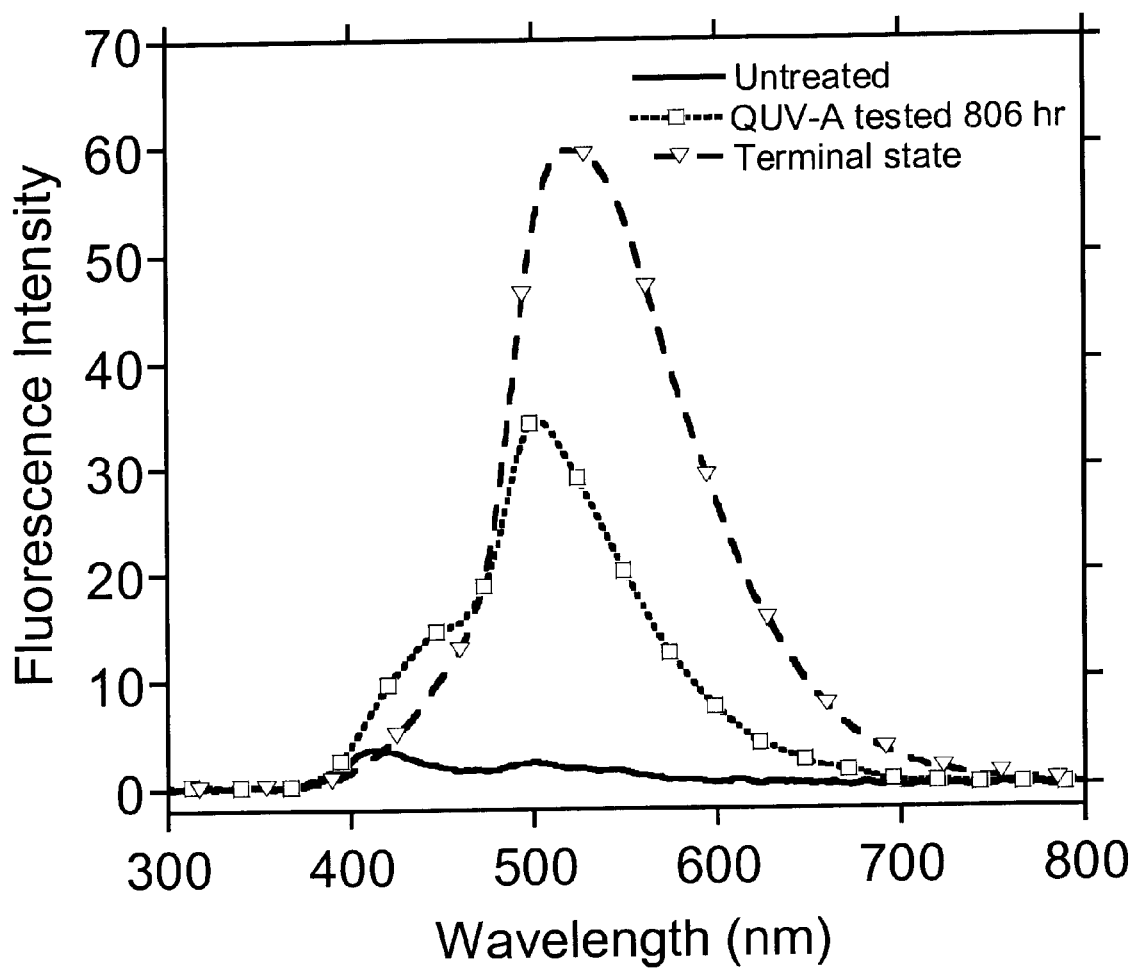
FIG. 4 is a plot of fluorescence intensity (photon counts) versus wavelength (nm) of the fluorescence emission spectra of a polycarbonate sample containing 2% rutile TiO$_2$ before exposure to UV radiation, after 806 h of exposure to UV radiation during a QUV test, and at its terminal state. Excitation wavelength in 340 nm.
Figure 5:
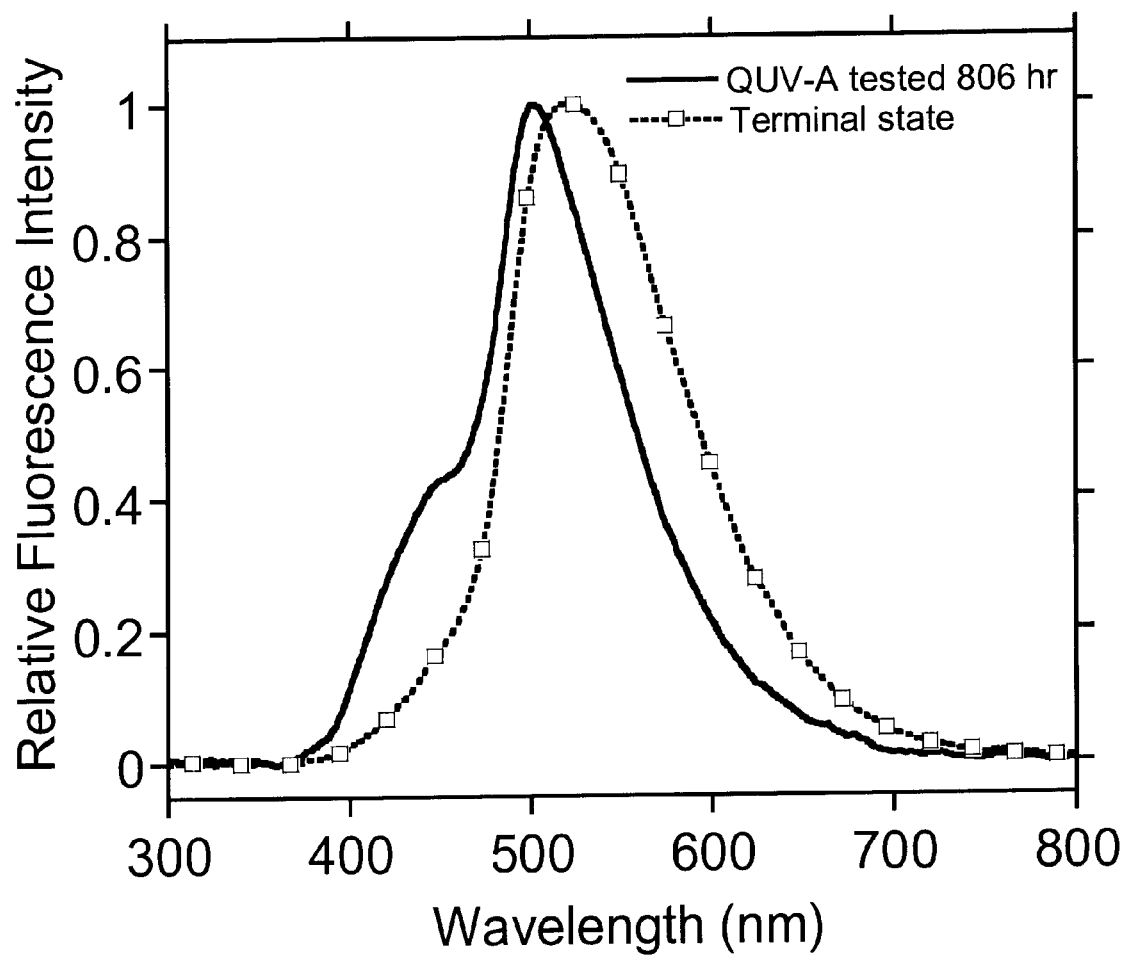
FIG. 5 is a plot of relative fluorescence intensity versus wavelength (nm) and represents a normalized fluorescence emission spectra of a polycarbonate sample containing 2% rutile TiO$_2$ after 806 h of exposure to UV radiation during a QUV test and at its terminal state. Excitation wavelength is 340 nm.

By taking a cross section of each of these spectra at a certain excitation wavelength, it is possible to quantify the increase in fluorescence signal upon material degradation. FIG. 4 illustrates fluorescence emission spectra of $PC+2\%TiO_2$ before exposure to UV radiation, after 806 h of exposure to UV radiation during a QUV test, and at its terminal state upon 340-nm excitation. Further, the spectral shifts of the fluorescence intensity. FIG. 5 demonstrates that the peak position exhibits a 20-nm red shift upon material degradation.

Unlike the measurements of YI, fluorescence measurements provide a broader range of parameters that can be correlated with the degradation of materials upon UV exposure. Measurements of a single or a combination of these variables can provide a more detailed description of the nature of the light-induced degradation of polymers or coatings.

EXAMPLE 2

Quantification of Material Degradation at Early Stages of UV Exposure.

Light-induced degradation of polymer materials at low exposure times was quantified by exciting fluorescence at 340 nm and measuring fluorescence intensity at 500 as the function of the exposure dose. The measurements were performed using a setup detailed in Example 1. The materials were Lexan® 140 polycarbonate containing 2% of TiO2 pigment prepared by standard extrusion and injection molding techniques. Samples were exposed in a xenon arc Weathero-meter® equipped with borosilicate inner and outer filters and operated according to ASTM G26-A procedure except that the irradiance was 0.75 $W/m^2$.

Figure 6:
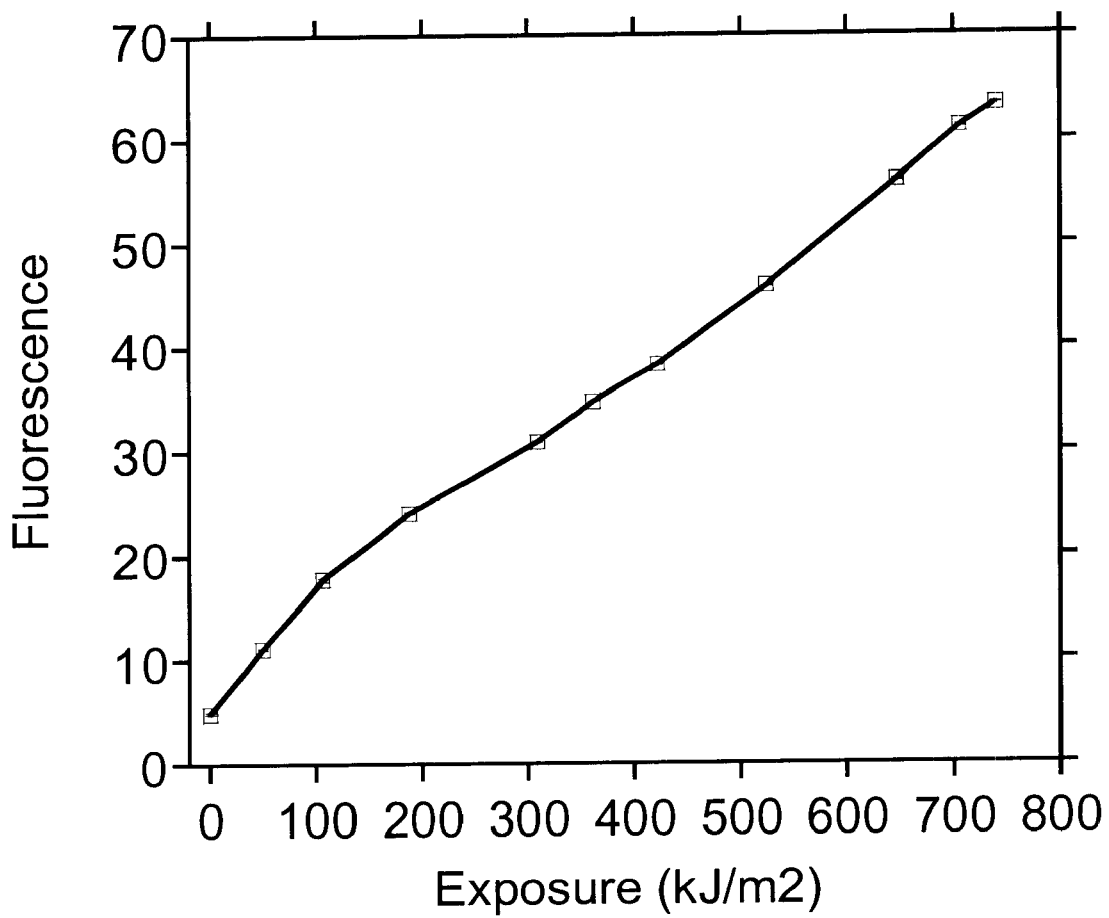
FIG. 6 is a plot of fluorescence versus exposure (kJ/m$^2$) in a xenon arc weatherometer equipped with a borosilicate inner and outer filters, of a polycarbonate sample containing 2% rutile TiO$_2$. This figure demonstrates the relation between the fluorescence intensity and the exposure dose. The smallest detectable change in the fluorescence signal (at a signal-to-noise ratio of three) corresponds to the exposure dose of 3.1 kJ/m$^2$ which, in turn, corresponds to 1.15 hours of exposure time, using this particular emission/detection instrumentation. Excitation wavelength, 340 nm, emission wavelength, 500 nm. Each data point is the mean of three measurements. Error bars (smaller than the data points) are one standard deviation. RSD over the measurement range, 0.2–1%.

FIG. 6 demonstrates the relation between the fluorescence intensity and the exposure dose. The smallest detectable change in the fluorescence signal (at the signal-to-noise ration of three) corresponds to the exposure dose of 3.1 kJ/m$^2$ which, in turn, corresponds to 1.15 hours of exposure time. Slight nonlinearity of the calibration curve is most likely due to the several competing degradation processes, associated with generation of several types of fluorescing species with different emission characteristics.

Figure 7:
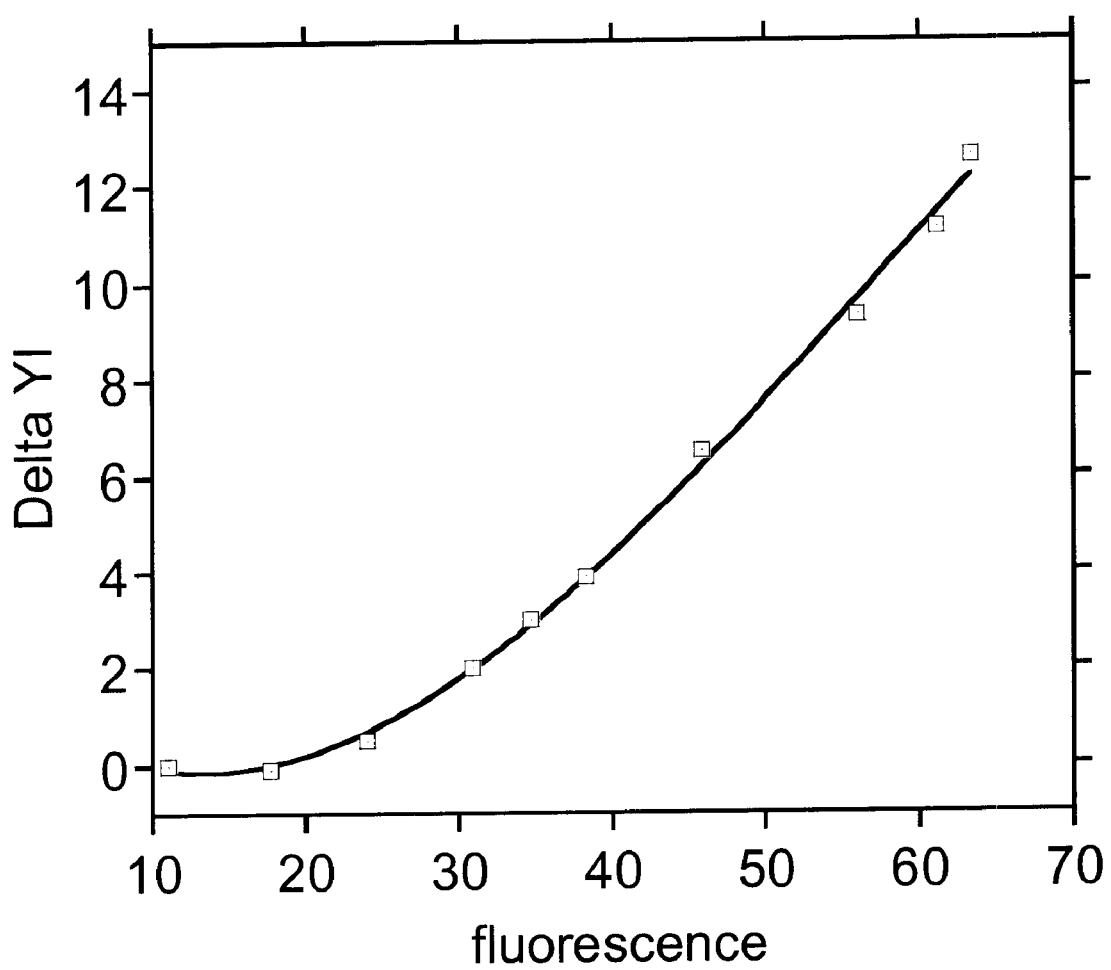
FIG. 7 is a plot of the delta (i.e., difference) of the YI versus fluorescence for a polycarbonate sample containing 2% rutile TiO$_2$. This data depicts the correlation between the measurement of YI and fluorescence. At low exposure dose, when YI is changing by only 1–2 units, fluorescence detection is clearly the method of choice because of its higher sensitivity.

FIG. 7 depicts the correlation between the measurement of YI and fluorescence. At low exposure does, when YI is changing only by 1–2 units, fluorescence detection is clearly the method of choice because of its higher sensitivity.

EXAMPLE 3

Degradation of Dark Color Weatherable Materials at Early Stages of UV Exposure.

Figure 8:
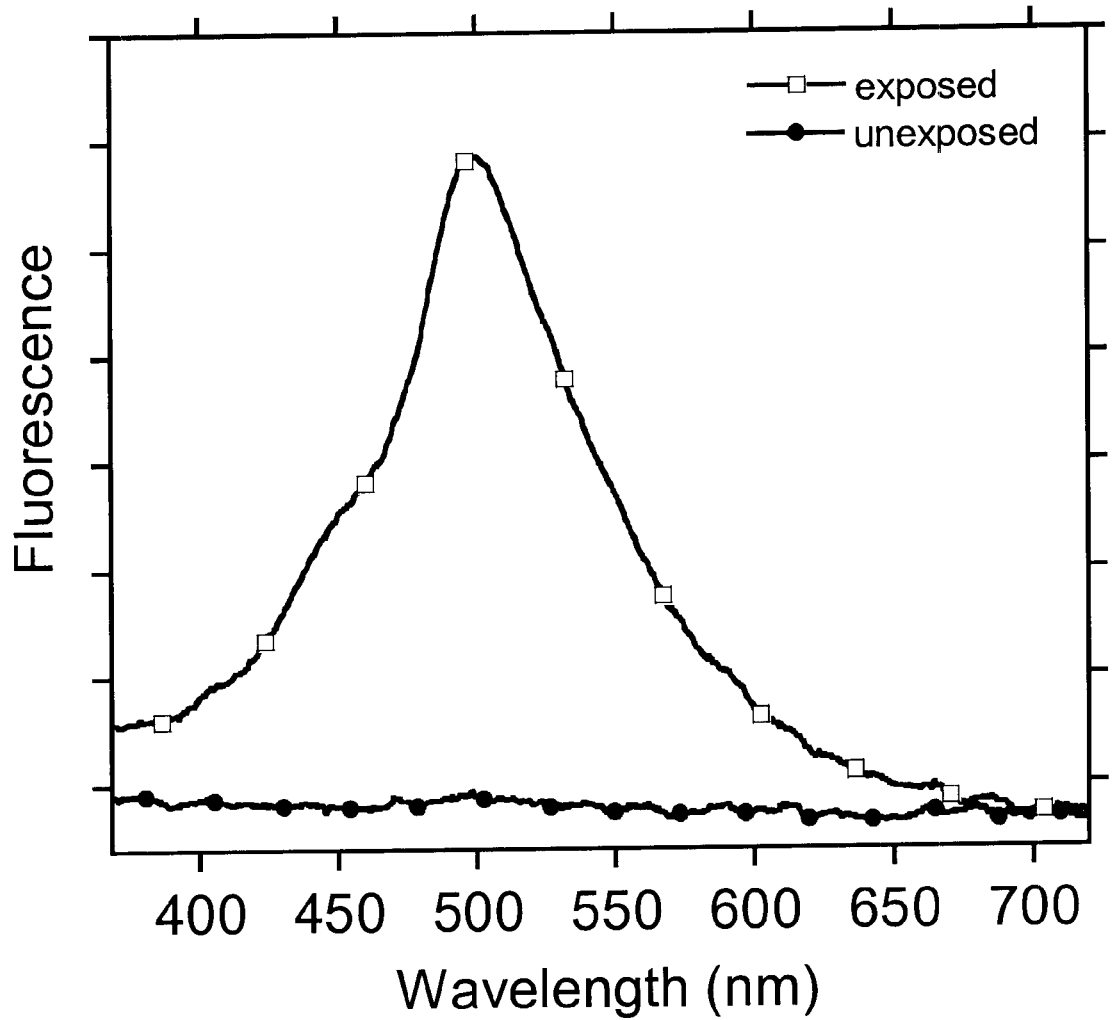
FIG. 8 is a plot of fluorescence versus wavelength of a polycarbonate (PC) and a poly(butylene terephthalate) (PBT) blend sample containing 0.6% carbon black before and after exposure to a 1600 kJ/m$^2$ dose of UV radiation. Excitation wavelength was 340 nm.
Figure 9:
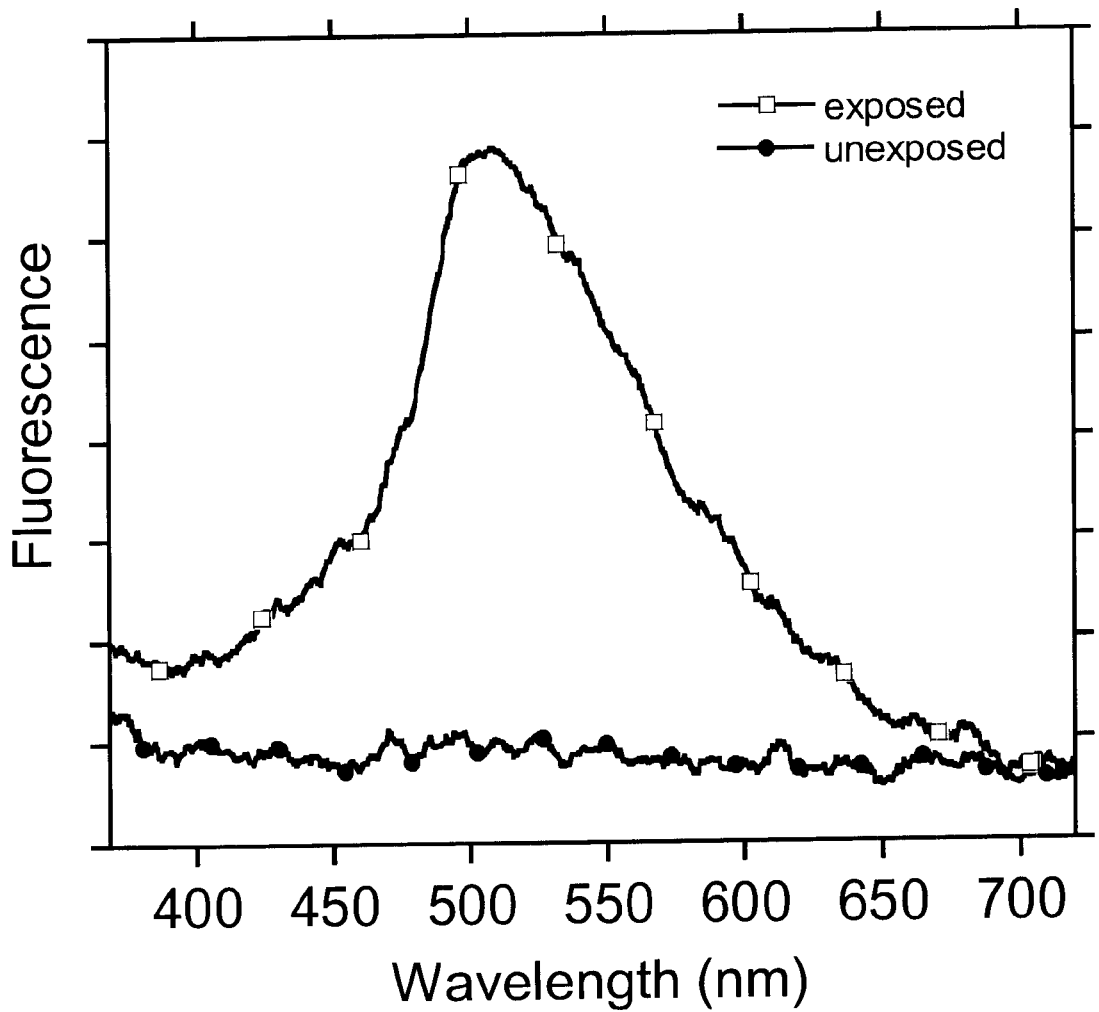
FIG. 9 is a plot of normalized fluorescence versus wavelength of a polycarbonate sample containing 0.6% carbon black before and after exposure to a 1600 kJ/m$^2$ dose of UV radiation. Excitation wavelength was 340 nm.

Degradation of black polymer materials was evaluated by fluorescence spectroscopy with the fluorescence excitation at 340 nm. Materials were PC with 0.6% carbon black and a blend of 45 parts of PC and 55 parts of PBT (PC/PBT) with 0.6% carbon black. All materials unexposed to UV light had negligible fluorescence upon excitation at 340 nm. After a 1600 kJ/m2 exposure to UV light in a xenon arc weatherometer, all materials had strong fluorescence as illustrated in FIGS. 8 and 9.

EXAMPLE 4

Analysis of Degradation Rate of Weatherable Materials with Different Pigments.

Degradation rate of different materials was evaluated upon addition of different pigments. Fluorescence intensity measurements were performed with an excitation at 340 nm. Studied materials were PC with 2% rutile TiO$_2$, PC with 0.6% carbon black, blend of 45 parts of PC and 55 parts of PBT (PC/PBT) with 2% rutile TiO$_2$, blend of 45 parts of PC and 55 parts of PBT (PC/PBT) with 0.6% carbon black, PBT with 2% rutile TiO$_2$, and PBT with 0.6% carbon black.

The exposure dose was varied from 0 to 1100 kJ/m2. Fluorescence of materials was measured as described in previous examples. Fluorescence intensity curves were normalized by their respective maxima values at high exposures and plotted for comparison in FIG. 10. Similar rates of the increase of fluorescence signal of the same materials but with different pigments demonstrate that pigment type does not affect degradation rate of materials.

EXAMPLE 5

Analysis of Libraries of Weatherable Materials.

For the high throughput screening of weatherability of diverse materials, a library of materials was arranged as a two-dimensional array. Material composition was changed as the first dimension and the exposure dose was changed as the second dimension.

Figure 11:
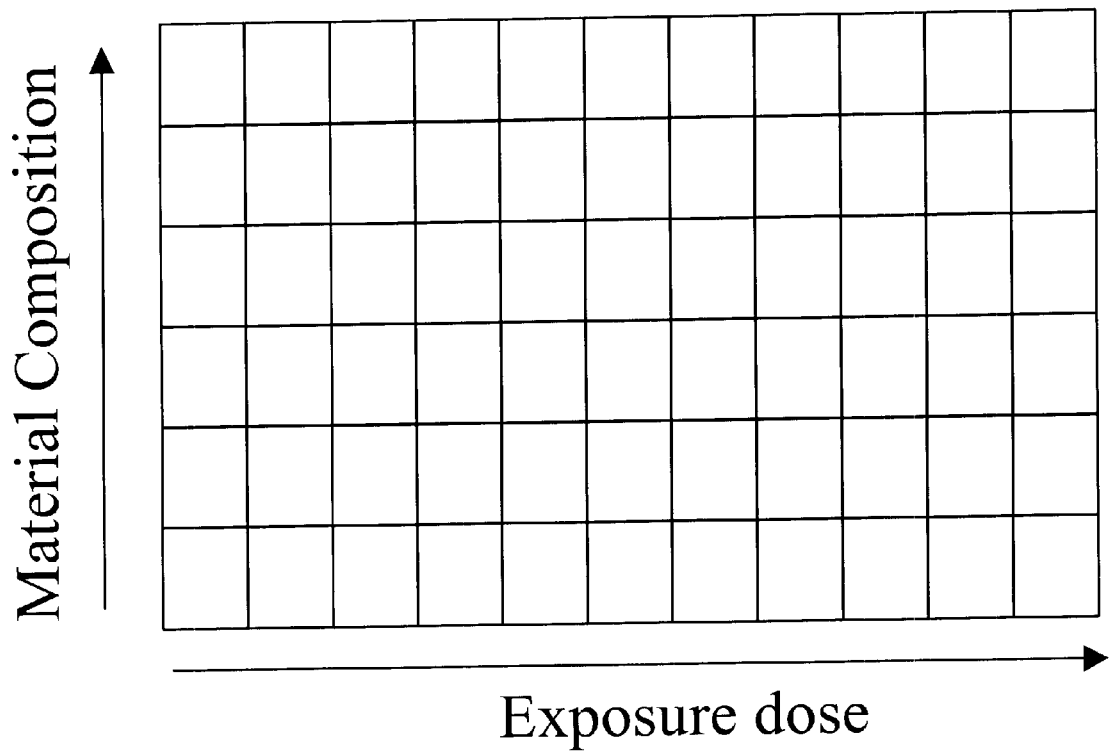
FIG. 11 is an illustration of an array of samples which could be analyzed using the methodology of this invention. This illustration shows the variation of material composition versus UV exposure dose.

Material composition included three polymers (PC, blend of 45 parts of PC and 55 parts of PBT (PC/PBT), and PBT) and two pigments (2% rutile TiO$_2$ and 0.6% carbon black). Exposure dose was varied from 0 to 1100 kJ/m2. Variation in exposure dose was produced by unmasking certain library members at predetermined time points. The library layout is shown in FIG. 11.

Figure 10:
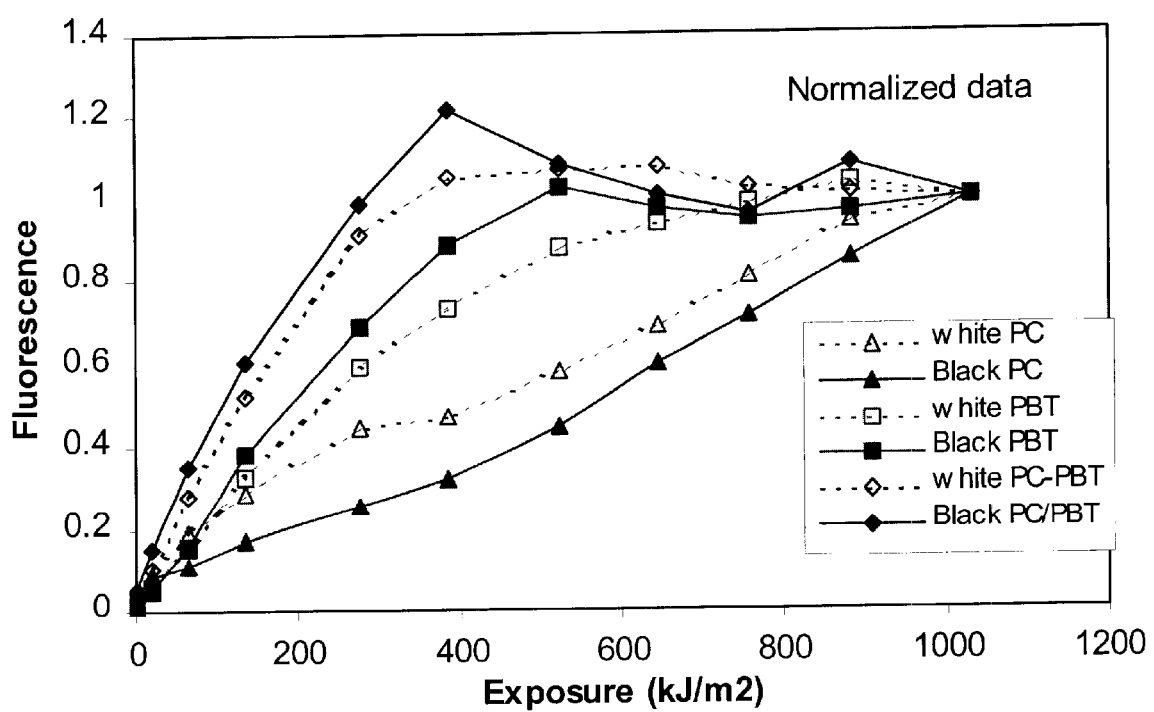
FIG. 10 is a plot of normalized fluorescence versus exposure in kJ/m$^2$. This data indicates that pigment type does not affect variation of the degradation rate. The open triangle points represent a white pigmented polycarbonate sample; the closed-triangle points represent a black pigmented polycarbonate sample, the open square points represent a white pigmented sample of poly(butylene terephthalate); the closed square points represent a black pigmented sample of poly(butylene terephthalate); the open diamond points represent a white pigmented polycarbonate-poly(butylene terephthalate) blend; and the closed diamond points represent a black pigmented polycarbonate-poly(butylene terephthalate) blend.

Fluorescence of materials was measured with an excitation at 340 nm as described in previous examples. FIG. 10 presents fluorescence intensity curves from the library arranged for the same material at different exposure doses and normalized by the respective maximum of fluorescence.

Fluorescence of the entire library was further obtained using an imaging detector such as a thermoelectrically cooled CCD Camera (Roper Scientific, 1100×330 pixels). Excitation of the fluorescence of the library was achieved using the same light source as used in previous examples. Fluorescence emission light was collected through a 500-nm interference filter with a band-pass of 10 nm. Imaging technique produced the same results compared to the sequential spectral measurements.

What is claimed is:

1. A method for determining the weatherability of at least one sample, wherein said sample(s) absorbs Visible and/or ultraviolet light and fluoresces visible, ultraviolet, and/or near infrared light, which comprises:

(a) exposing said sample to visible and/or ultraviolet radiation while compiling fluorescence emission spectral data from said sample over a period of time beginning after initial exposure; and (b) applying a predetermined selection test to said spectral data so as to indicate which of the samples exhibit a desired resistance to ultraviolet radiation-induced degradation.

2. The method of claim 1, further comprising the step of calculating useful lifetime of a given material based on said spectral data.

3. The method of claim 1, wherein the visible and/or ultraviolet light is of a wavelength of greater than 295 nm.

4. The method of claim 1, wherein said sample is comprised of a thermoplastic or thermoset resin.

5. The method of claim 4, wherein the resin is selected from the group consisting of polycarbonates, polyesters, polystyrenes, styrene-acrylonitrile (SAN) copolymers, acrylonitrile-butadiene-styrene copolymers (ABS), acrylonitrile-styrene-acrylate copolymers (ASA), polyarylates, and blends thereof.

6. The method of claim 1, wherein the sample comprises of at least one pigment.

7. The method of claim 6, wherein the pigment is selected from the group consisting of titanium dioxide, carbon black, phthalocyanines, and iron oxides.

8. The method of claim 1, wherein said samples are in the form of an array.

9. A method for determining weatherability of at least one sample, wherein said sample absorbs visible and/or ultraviolet light and fluoresces visible, ultraviolet, and/or near infrared light, which comprises:

(a) exposing said sample to ultraviolet radiation while compiling fluorescence emission spectral data from said sample over a period of time beginning after initial exposure; and (b) applying a pre-determined selection test to said spectral data so as to indicate which of the samples exhibits the least amount of increase of fluorescence intensity or slowest rate of fluorescence increase.

10. The method of claim 9, wherein the ultraviolet light is of a wavelength of greater than 295 nm.

11. The method of claim 9, wherein said sample is comprised of a thermoplastic or thermoset resin.

12. The method of claim 11, wherein the resin is selected from the group consisting of polycarbonates, polyesters, polystyrenes, styrene-acrylonitrile (SAN) copolymers, acrylonitrile-butadiene-styrene copolymers (ABS), acrylonitrile-styrene-acrylate copolymers (ASA), polyarylates, and blends thereof.

13. The method of claim 12, wherein the sample comprises at least one pigment.

14. The method of claim 13, wherein the pigment is selected from the group consisting of titanium dioxide, carbon black, phthalocyanines, and iron oxides.

15. The method of claim 9, wherein said samples are in the form of an array.

16. A method for determining weatherability of at least one sample, wherein said sample absorbs visible and/or ultraviolet light and fluoresces visible, ultraviolet, and/or near infrared light, which comprises:

(a) exposing said sample to ultraviolet radiation while compiling fluorescence emission spectral data from said sample over a period of time beginning after initial exposure; and (b) applying a pre-determined selection test to said spectral data so as to indicate which of the samples exhibits the least amount of change in fluorescence stokes shift.

17. The method of claim 16, wherein the ultraviolet light is of a wavelength of greater than 295 nm.

18. The method of claim 16, wherein said sample is comprised of a thermoplastic or thermoset resin.

19. The method of claim 18, wherein the resin is selected from the group consisting of polycarbonates, polyesters, polystyrenes, styrene-acrylonitrile (SAN) copolymers, acrylonitrile-butadiene-styrene copolymers (ABS), acrylonitrile-styrene-acrylate copolymers (ASA), polyarylates, and blends thereof.

20. The method of claim 16, wherein the resin is comprised of at least one pigment.

21. The method of claim 20, wherein the pigment is selected from the group consisting of titanium dioxide, carbon black, phthalocyanines, and iron oxides.

22. The method of claim 16, wherein said samples are in the form of an array.

* * * * *